United States Patent [19]

Nickell

[11] 3,992,190

[45] Nov. 16, 1976

[54] CHEMICAL RIPENING OF SUGARCANE USING ALKYLARSINIC ACID COMPOUNDS

[75] Inventor: Louis G. Nickell, Honolulu, Hawaii

[73] Assignee: Hawaiian Sugar Planters' Association, Honolulu, Hawaii

[22] Filed: Apr. 17, 1975

[21] Appl. No.: 569,074

[52] U.S. Cl. .................................... 71/97; 71/76
[51] Int. Cl.² .................................... A01N 11/08
[58] Field of Search ................................ 71/76, 97

[56] References Cited
UNITED STATES PATENTS 3,697,253   10/1972   MacMurray ........................... 71/97

Primary Examiner—Lewis Gotta
Assistant Examiner—Catherine L. Mills
Attorney, Agent, or Firm—Burns, Doane, Swecker & Mathis

[57] ABSTRACT

Sucrose yield of sugarcane is increased by treating the cane crop a few weeks prior to harvest with a ripening agent comprising an alkylarsinic acid such as monomethylarsinic or dimethylarsinic acid or higher homologs thereof, or their salts.

10 Claims, No Drawings

CHEMICAL RIPENING OF SUGARCANE USING ALKYLARSINIC ACID COMPOUNDS

FIELD OF THE INVENTION

This invention relates to an improvement in the production of sugar from sugarcane. More particularly, it relates to a process for increasing the sugar yield of sugarcane by the application of cacodylic acid or other mono- or dialkylarsinic acids, or salts thereof, to the maturing sugarcane plants in the field a few weeks prior to harvest.

THE PRIOR ART

A number of chemical ripeners for sugarcane has been previously proposed. Some of these are disclosed, for example, in U.S. Pat. Nos. 3,224,865; 3,245,775; 3,291,592; 3,482,959; 3,482,961; 3,493,361; 3,505,056; 3,660,072 and 3,671,219. Still other chemical agents which have been found successful or shown promise as sugarcane ripeners, such as cyclo-leucine, anisomycin and cycloheximide, are disclosed, for instance, in Hawaiian Planters' Record, Vol. 58, No. 5, pp. 71–79 (1970).

The more active ripeners differ widely from each other in terms of chemical structure as well as chemical and biological properties. Some are known growth stimulants, others are known growth retardants, weed killers, active antibiotics and so on, but the vast majority of compounds in all of these classes are of no value as sugarcane ripeners. In the search for effective ripeners failures continue to outnumber successes by a wide margin, and as of this date there is still no known screening test for determining the ripening activity of a compound other than to test it on maturing sugarcane. Because of toxicological or ecological concerns and the consequent possibility that rotation of use of different chemical ripeners in consecutive seasons in a given area may be preferable to the continued use of a single ripener or ripener mixture, the search for new sugarcane ripeners continues unabated.

OBJECTS OF THE INVENTION

It is an object of this invention to provide new and economically useful chemical ripening agents for sugarcane. A more general object is to increase the sucrose yield of sugarcane by chemically treating it during its maturation prior to harvest without introducing objectionable toxicological hazards. More specifically, it is an object of this invention to increase the sucrose yield of maturing sugarcane by treating a cane crop nearing its normal harvest time with cacodylic acid or with a similar mono- or dialkylarsinic acid or with a salt thereof. The compounds useful in the present invention are sufficiently stable to provide the desired effect over a period of several weeks between application and a variable harvest date, but yet have a relatively low degree of persistence. Compounds which increase the sucrose content only temporarily over a period of three weeks or less after application and then result in a substantial decrease are usually not desirable chemical ripeners except in situations where harvesting time can be rigidly programmed in advance in relation to the time of application of the chemical ripener.

SUMMARY OF THE INVENTION

According to the present invention the desired objectives have been achieved by the application of ripening compositions comprising, specifically, cacodylic acid (dimethylarsinic acid) or a salt thereof, or, more broadly, an alkylarsinic acid or salt corresponding to the formula

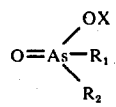

wherein X is hydrogen, ammonium, an alkali metal or an alkaline earth metal, $R_1$ is hydroxyl, methyl, ethyl, propyl, butyl or allyl, and $R_2$ is methyl, ethyl, propyl, butyl or allyl. More specifically, an excellent increase in sucrose yield has been obtained by applying a spray or dust comprising one or more of such compounds to maturing sugarcane stalks in a crop near the end of its normal maturation cycle, and harvesting such a crop some weeks later. The composition is applied directly to the stalks by spraying, dusting or the like in order that it be deposited on the stalks including the younger, growing parts thereof. The normal maturation cycle of sugarcane under conditions such as those prevailing in Hawaii is from about 18 to about 36 months, though in some areas sugarcane is ripe and ready for harvest in 9 to 12 months.

The preferred usage form is a mixture containing the alkylarsinic acid compound in an aqueous solution or suspension utilizing one or a combination of known surface active agents commonly and variously used in the prior art as wetting agents, detergents or emulsifying agents. However, dry dusting compositions containing the alkylarsinic acid compound and a solid diluent such as clay are also useful.

Cacodylic acid and the other compounds useful for the purposes of this invention are per se well known in the art and have been previously proposed for use as herbicides or defoliants. See, for instance, U.S. Pat. Nos. 3,056,668; 3,254,982 and 3,378,364, which disclose a variety of dialkylarsinic acids and their salts; and U.S. Pat. No. 2,678,265, which discloses monoalkyl substituted arsenic acids and their salts. All these acids form salts with bases such as sodium, potassium, calcium, aluminum or ammonium hydroxide. Both the free acids and their salts may be used in the present invention. However, while the compounds have for many years past been widely used in agriculture and horticulture as herbicides, defoliants or the like, their application to sugarcane for the purpose of increasing its sucrose yield has not been previously suggested and their high effectiveness for this purpose is surprising.

Cacodylic acid and sodium cacodylate are particularly useful. Other useful compounds include, for instance, diethylarsinic acid, methylethylarsinic acid, dibutylarsinic acid, diallylarsinic acid, methylarsonic acid, mixtures thereof, as well as the salts thereof, especially their water-soluble salts, e.g., disodium butylarsonate.

In accordance with this invention, a sugarcane crop which is nearing the normal maturity stage, e.g., a crop in Hawaii which is 18 to 36 months of age, is treated with cacodylic acid or a similar hydrocarbon substituted arsenic acid, or with a mixture containing one or more such compounds, about two to ten weeks before harvest, the preferred time for treatment being between about 5 to 8 weeks prior to harvest.

Good results are obtained when the sugarcane crop is treated in the field at a rate in the range of from 1 to 4 pounds per acre (1 to 4 kg/hectare) of the active acid or salt. However, higher rates, e.g., up to about 30 pounds per acre (about 30 kg/hectare) of the chemical ripener, or rates lower than 1 pound per acre (1 kg/hectare) can also be used. One acre, it may be noted, equals about 0.405 hectares. The optimum amount will vary somewhat depending on the particular mode of application, environmental conditions, time of year, and age and variety of cane being treated, but can be readily determined for each particular case by preliminary testing.

The active agent is conveniently applied in the field in the form of an aqueous solution, emulsion or suspension, i.e., in a liquid composition which may be sprayed onto the maturing cane plants from a boom-spray, or it can be dusted on from an airplane or the like as a dust composition which contains the active compound diluted with an inert solid such as clay.

In preparing suitable liquid compositions, surface active agents of the type described, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethyleneoxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the active ripener to the sugarcane field in the form of an aqueous solution, suspension or emulsion having a concentration of active agent such that the application at the rate of from 5 to 20 gallons per acre (about 50 to 200 liters per hectare) of liquid composition will provide the required dosage of active chemical. However, the use of lower or higher rates may be preferred when a different dispensing mechanism is used.

The preferred carrier for the active ripening agent is water to which about 0.1 to 2% by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the ripening agents of the present invention constitute essentially the sole active ingredient in the treating composition, but they may also be applied in combination with other agents.

DESCRIPTION OF SPECIFIC EMBODIMENTS

EXAMPLE 1

Part A - Preparation of Treating Compositions a. A treating composition is prepared by weighing out 1 gram of dimethylarsinic acid (cacodylic acid) and dissolving it in approximately 6 ml of water. This solution is diluted with water to exactly 8 ml, 1 drop of commercial Tergitol NPX (liquid) surfactant is added with a medicine dropper to the diluted acid solution. The solution is agitated by shaking prior to application.

b. A similar composition is prepared in the same manner as described above, using sodium cacodylate in lieu of free cacodylic acid.

Part B - Application of Cacodylic Acid Composition to Cane

A 0.3 ml dose of the aqueous solution containing 38 mg cacodylic acid, prepared as described under (a) in Part A above, was applied on the spindle area at the top of the last visible dewlap of each of 20 stalks of sugarcane in a test plot in a commercial cane field in Hawaii, using a syringe with a fine needle as a microapplicator.

Other groups of 20 stalks each in the same test plot were treated in an identical manner for comparative purposes (a) with the cacodylic acid solution at half strength (.19 mg/stalk), (b) with the sodium cacodylate solution at a dosage of 38 mg/stalk, (c) with the sodium cacodylate solution at a dosage of 19 mg/stalk, and (d) with "Trysben" (dimethylamine salt of 2,3,6-trichlorobenzoic acid), used as a standard because of its known and consistent good activity.

The age of the cane at the time of application was 14–25 months.

A set of 10 of these treated stalks from each group were harvested four weeks after such treatment and another set of 10 were harvested 5 weeks after such treatment. At each harvest a set of 10 untreated stalks from the same plot were also harvested as a control.

The top 15 joints of each 10-stalk set of the treated stalks, as well as those of untreated control stalks from the same test plot, were removed, and each set was combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The test data are given in Table I.

The data show that treatment with cacodylic acid and with sodium cacodylate brings about a substantial increase in sucrose yield as compared with the untreated cane when an adequate dosage of cacodylic acid or salt is applied.

EXAMPLE 2

Using the same procedure as that described above in Example 1, similar tests were conducted at later times with different varieties of cane. The test data are shown in Tables IIA, IIB and IIC.

Referring to Tables IIA, IIB and IIC, it can be seen from each that cacodylic acid and sodium cacodylate show at least the same degree of effectiveness as Trysben and in most instances show a distinct superiority over Trysben. The improvement is particularly conspicuous when the ripeners are applied to the cane 5 weeks prior to harvest.

TABLE I

| Cane Variety: | 57-4510 Field I |
| Age: | 14.25 months |
| Date of Treatment: | December 17, Year Y |
| Dates of Harvest: | January 15 and 21, Year Y + 1 |

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Cacodylic Acid | | | | |

TABLE I-continued

| | | | | |
|---|---|---|---|---|
| 38 mg/stalk | 84.77 | 14.86 | 83.29 | 13.41 |
| 19 mg/stalk | 75.92 | 10.75 | 84.11 | 13.71 |
| Sodium Cacodylate | | | | |
| 38 mg/stalk | 85.18 | 13.91 | 84.67 | 13.92 |
| 19 mg/stalk | 78.05 | 11.95 | 75.31 | 11.07 |
| Trysben (standard) | 75.92 | 10.94 | 82.74 | 13.47 |
| Control (untreated) | 77.80 | 11.21 | 75.59 | 10.16 |

TABLE IIA

Cane Variety: 49-3533 Field II
Age: 21.5 months
Date of Treatment: February 15, Year Y + 1
Dates of Harvest: March 17 and March 24, Year Y + 1

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Cacodylic Acid, 19 mg/stalk | 82.35 | 11.86 | 88.34 | 12.86 |
| Sodium Cacodylate, 38 mg/stalk | 80.08 | 10.14 | 88.71 | 13.70 |
| Trysben (standard) | 81.31 | 11.03 | 85.04 | 12.21 |
| Control (untreated) | 81.69 | 11.20 | 78.50 | 9.58 |

TABLE IIB

Cane Variety: 59-3775 Field III
Date of Treatment: May 11, Year Y + 2
Dates of Harvest: June 8 and 15, Year Y + 2

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Cacodylic Acid, 38 mg/stalk | 78.25 | 10.38 | 79.07 | 11.48 |
| Sodium Cacodylate, 38 mg/stalk | 79.55 | 11.02 | 79.78 | 10.98 |
| Trysben (standard) | 74.52 | 8.87 | 73.86 | 9.61 |
| Control (untreated) | 74.25 | 8.28 | 70.66 | 7.38 |

TABLE IIC

Cane Variety: 59-3775 Field IV
Age: 20.25 months
Date of Treatment: May 14, Year Y + 3
Dates of Harvest: June 10 and 17, Year Y + 3

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Cacodylic Acid, 38 mg/stalk | 78.49 | 10.27 | 82.64 | 12.17 |
| Cacodylic Acid, 19 mg/stalk | 75.44 | 9.91 | 83.67 | 12.39 |
| Sodium Cacodylate, 38 mg/stalk | 78.06 | 9.85 | 80.36 | 11.17 |
| Sodium Cacodylate, 19 mg/stalk | 78.68 | 10.08 | 83.16 | 11.80 |
| Trysben (standard) | 78.34 | 10.84 | 80.28 | 11.22 |
| Control (untreated) | 71.56 | 8.15 | 70.66 | 7.43 |

The tabulated data show that in each test series cacodylic acid produces a very important increase in sucrose yield over that obtained in the untreated control.

The nature, scope, utility and effectiveness of the present invention have been described and exemplified in the foregoing specification. However, these examples are not intended to be limiting. The true scope of the invention which is to be protected by patent is particularly pointed out in the appended claims.

What is claimed is:

1. A process for modifying the ripening of field grown sugarcane plants so as to increase their yield of sucrose which comprises applying to maturing cane plants at a time from 2 to 10 weeks prior to harvest a sucrose increasing amount of cacodylic acid, sodium cacodylate or mixtures thereof.

2. A process according to claim 1 wherein said ripening agent is sprayed onto the cane plants as a liquid composition containing water as a carrier.

3. A process according to claim 2 wherein the aqueous composition contains between 0.1 and 2% by weight of a surface active agent.

4. A process according to claim 2 wherein the aqueous composition contains between 0.1 and 2% by weight of a nonionic surface active agent.

5. A process according to claim 1 wherein said ripening agent is cacodylic acid.

6. A process according to claim 5 wherein said cacodylic acid is applied to the cane plants at the rate of about 1 to 4 pounds per acre about 5 to 8 weeks prior to harvest.

7. A process according to claim 1 wherein said ripening agent is sodium cacodylate.

8. A process according to claim 5 wherein the cacodylic acid is applied to the plants as an aqueous solution.

9. A process according to claim 1 wherein the sodium cacodylate is applied to the plants as an aqueous solution.

10. A process according to claim 1 wherein the cane plants are between 18 and 36 months of age when the ripening agent is applied thereto.

* * * * *